United States Patent [19]

Willmitzer et al.

[11] Patent Number: 5,436,394
[45] Date of Patent: Jul. 25, 1995

[54] PLASMID FOR THE PREPARATION OF TRANSGENIC PLANTS WITH A CHANGE IN HABIT AND YIELD

[75] Inventors: Lothar Willmitzer; Uwe Sonnewald, both of Berlin; Antje Von Schaeven, Belau, all of Germany

[73] Assignee: Schering Aktiengesellschaft, Berlin, Germany

[21] Appl. No.: 156,876

[22] Filed: Nov. 23, 1993

Related U.S. Application Data

[63] Continuation of Ser. No. 653,689, Feb. 11, 1991, abandoned.

[30] Foreign Application Priority Data

Feb. 13, 1990 [DE] Germany .................. 40 04 800.4

[51] Int. Cl.⁶ .................. A01H 1/00; A01H 5/00; C12N 15/82; C12N 5/14
[52] U.S. Cl. ................... 800/205; 800/DIG. 42; 435/69.8; 435/320.1; 435/201; 435/240.4; 435/172.3; 47/58
[58] Field of Search ............. 800/205, DIG. 42; 435/172.3, 240.4, 320.1, 69.8, 201; 935/27, 30, 48, 67; 47/58

[56] References Cited

U.S. PATENT DOCUMENTS 4,771,002 9/1988 Gelvin .................. 435/172.3
4,801,540 1/1989 Hiatt et al. .

FOREIGN PATENT DOCUMENTS 0438904 7/1991 European Pat. Off. .
8809334 12/1988 WIPO .
8912386 12/1989 WIPO .

OTHER PUBLICATIONS

Parrick, J. W. Physiologia Plantarum, vol. 78 (1990) 298–308.
Dickinson, C. D., et al. Plant Physiology, vol. 95 (1991) 420–425 (Abstract).
Thorne, J. H. Ann. Rev. Plant Physiology, vol. 36 (1985) pp. 317–343.
Stitt, M., et al. Physiologia Plantarum, vol. 77 (1989) pp. 633–641.
Sheerman, S., et al. Plant Cell Reports, vol. 7 (1988) pp. 13–16.
Rocha-Sosa, M., et al. EMBO J., vol. 8, (1989) pp. 23–29.
Taussig, R, et al. Nucleic Acids Research, vol. 11 (1983) pp. 1943–1954.
Dorel, C., et al.—Abstract Plant Physiology, vol. 86 (4 Suppl.) (1988) p. 84.
Gielen, J., et al. EMBO J., vol. 3 (1984) pp. 835–846.
Jefferson, R., et al. EMBO J., vol. 6 (1987) pp. 3901–3907.
Stockhaus, J., et al. P.N.A.S. vol. 84 (1987) pp. 7943–7947.
Keil, M., et al. Nucleic Acids Research, vol. 14, (1986) pp. 5641–5651.
Rosahl, S., et al. Mol. Gen. Genet., vol. 203 (1986) pp. 214–220.

(List continued on next page.)

Primary Examiner—David T. Fox
Assistant Examiner—Charles Rories
Attorney, Agent, or Firm—Ostrolenk, Faber, Gerb & Soffen

[57] ABSTRACT

There is disclosed plasmids for the preparation of transgenic plants, as well as the plants, that are modified through the transfer and the expression of genes influencing the sugar metabolism or the sugar partitioning within a plant, which are localised on these plasmids.

The transferred genes cause a modified distribution of assimilates in the transgenic plant which result in significant changes in habit, such as size, leaf shape, internode separation and root formation, as well as improvements in yield.

Plasmids are also described which enable foreign proteins to be directed into the vacuoles of transgenic plants.

12 Claims, 6 Drawing Sheets

OTHER PUBLICATIONS

Devlin, R., Plant Physiology, 3rd Ed., N.Y., D. Van Nostrand Co., 1975 pp. 16, 204–206.

UCLA Symp. Mol. Cell. Biol., New Ser., vol. 129, 1990 (Plant Gene Transfer), Proceedings of a UCLA Symposium, 1.–7. Apr. 1989, Park City, Utah, pp. 225–236, Wiley-Liss—A John Wiley & Sons, Inc. Publication, New York, US; B. W. Tague et al.: "Identification of a vacuolar targeting domain using transgenic yeast and tobacco".

Cell, vol. 48, 13. Mar. 1987, pp. 875–885, Cell Press; L. M. Johnson et al.: "Distinct sequence determinants direct intracellular sorting and modification of a yeast vacuolar protease".

The EMBO Journal, vol. 9, No. 10, Oct. 1990, pp. 3033–3044, Oxford University Press; A. von Schaewen et al.: "Expression of a yeast–derived invertase in the cell wall of tobacco and Arabidopsis plants leads to accumulation of carbohydrate and inhibition of photosynthesis and strongly influences growth and phenotype of transgenic tobacco plants".

FRESH WEIGHT

5,436,394

PLASMID FOR THE PREPARATION OF TRANSGENIC PLANTS WITH A CHANGE IN HABIT AND YIELD

This is a continuation of application Ser. No. 07/653,689 filed on Feb. 11, 1991, now abandoned.

The present invention relates to new plasmids for the preparation of transgenic plants, as well as the plants, that are modified through the transfer and the expression of genes influencing the sugar metabolism or the sugar partitioning within a plant, which are localised on these plasmids.

BACKGROUND OF THE INVENTION

The growth, the development and the yield of a crop or an ornamental plant depends on the energy that the plant gains through the fixing of $CO_2$ in carbohydrates during photosynthesis. The primary loci for photosynthesis are the leaves and to a lesser extent the stem tissue, whereas other organs of the plant, such as roots, seeds or tubers, do not make a material contribution to the formation of photoassimilates, but on the contrary are dependent for their growth on the supply from photosynthetically active organs. This means that there is a flow in photosynthetically gained energy from photosynthetically active tissues to photosynthetically inactive parts of a plant.

The photosynthetically active tissues are designated as sources. They are defined as net exporters of the fixed carbon dioxide. The photosynthetically inactive parts of a plant are designated as sinks. They are defined as net importers of the photosynthetically fixed carbon dioxide.

It is believed that the sinks have a strong influence in several ways both in the efficient use of photosynthetic products as well in their distribution within a plant. One example is the habit of the plant. Newly developing organs, such as very young leaves or other areas such as roots and seeds, are fully dependent on the photosynthesis performance of the sources. That means that the development of such organs is dependent on the distribution of the photoassimilates formed from the sources within the plants. The possibility of the formation of young leaves or also the formation of roots can have drastic effects on the habit of a plant, such as for example the size of a plant, the internode separation, the size and shape of a leaf, the appearance of a leaf and the number and shape of the roots. Further, the distribution of photoassimilates would have quite critical meaning for the yield of a plant. Whilst, in the last decades, the harvestable yield of a wheat plants has increased, the total photosynthesis performance of wheat has not changed significantly. This is explained by the sink to source relationship being changed in such a way that the sinks which are important for the yield, such as seeds, take up essentially more photoassimilates than other parts of the plant which are unimportant as far as yield is concerned, such as the stem. In this case, through a shortening of the stem, a much more valid sink to source relationship in wheat could be achieved. This underlines the importance of the distribution of photoassimilates in higher plants formed in the primary sources in relation to both the habit and also the yield of plants.

It is not known through which biochemical mechanism the relationship of sink and source is regulated.

New biotechnological processes for the genetic change of dicotyledonous and monocotyledonous plants are known (Gasser and Fraley, 1989, Science 244, 1293–1299).

In most plants, photoassimilates are distributed within a plant in the form of sugars and preferentially in the form of sucrose. The distribution of sucrose between source and sink tissues occurs by transport of sucrose via the phloem. One of the important determinants for the strength of a sink could be the unloading of the phloem in the sink. In order to achieve a strong unloading of sucrose from the phloem into the sink, the sucrose should be transformed as soon as possible after leaving the phloem into a different chemical component that no longer has a chemical relationship to sucrose.

Changes of the plant habit mean important improvements in known plants. For example, this can lead to a shortening of the stem to give varieties which have greater wind resistance. A preferable distribution of the photoassimilates in harvestable organs such as seeds, eg of barley, wheat, soya beans or maize; leaves, for example tobacco; stems, for example sugar cane; tubers, for example potatoes; beets, for example animal feed beets and sugar beet; and fruit, for example tomatoes, should lead to a higher yield of a plant. These changes apply also to ornamental and garden plants which lead to plants with a completely new habit.

SUMMARY OF THE INVENTION

The object of the present invention is to provide plasmids for the preparation of plants which are changed in their habit such as size, leaf shape, internode separation and root formation as well as in their harvestable yield. A further object of the invention is the provision of plants containing these plasmids.

It has now been found that plasmids, on which genes are located that influence the sugar metabolism or the sugar partitioning, after targeted introduction in the plants, are expressed in these transgenic plants whereby the coded products lead to a changed distribution of photoassimilates in these transgenic plants. In this way, it has been shown surprisingly that the introduction of individual genes leads to significant modifications in the habit and yield.

Especially important changes in the habit and yield of plants, such as for example of potato and tobacco plants, can be achieved with plasmids that contain the DNA sequences of a gene of a sucrose-modifying enzyme, whereby this gene is an invertase gene, such as for example the invertase gene suc2 from yeast, and whereby the sequences of this gene are fused to the regulating regions of other genes, that ensure an expression of the invertase gene in plant cells and plants, as well as optionally in a DNA sequence, that ensures the direction of the invertase protein in vacuoles of the plant and plant cells.

The DNA sequence of the invertase gene can optionally be placed adjacent a further DNA sequence that is fused onto a signal peptide necessary for the uptake in the endoplasmic reticulum of plants and plant cells. The regulatory regions here, are promoters and termination signals of plant genes. Promoters that can be used are those which have an approximate constitutive expression, such as for example the 35 S promoter RNA cauliflower mosaic virus, and those which have an expression only in specified tissues, such as in photosynthetically active cells, such as for example the promoter of the ST-LS1 gene or in storage sinks, such as tubers, beets or fruits, such as for example the promoter of the class I-Patatin gene B33 or in storage sinks such as seeds, for example seed specific expressed promoters.

Signal peptides that can be used are for example proteinase inhibitor II-gene from *Solanum tuberosum*, in which the signal peptide can be optionally fused with parts of another gene, such as for example the octopine-synthase gene.

The DNA sequence that ensures the direction of foreign proteins, such as for example of the invertase protein in vacuoles of the plant and plant cells, can be for example a DNA sequence of the patatin gene pgT5 from *Solanum tuberosum*. The DNA sequence that ensures the direction of the foreign protein in vacuoles leads as a rule to a fusion product with the foreign protein.

For the introduction of foreign genes into higher plants, a large number of cloning vectors are available, which include a replication system in *E. coli* and a marker which allows a selection of the transformed cells. The vectors include for example pBR 332, pUC series, M13 mp series, pACYC 184, etc. Accordingly the sequence can be introduced in a suitable restriction position in the vector. The plasmid is obtained for transformation in *E. coli*. The *E. coli* cells are cultivated in a suitable nutrient medium and then harvested and lysed. The plasmid is recovered. In general, for analysis, a sequence analysis, restriction analysis, electrophoresis and further biochemical-molecular biological methods are carried out. After each manipulation, the DNA sequence, which is used, can be cleaved and joined to the next DNA sequence. Each plasmid sequence can be cloned in the same or different plasmids. According to each method of introducing the desired gene into the plants, further DNA sequences could be necessary. Should, for example the Ti- or Ri-plasmid be used for the transformation of the plant cells, so that at least the right border, often however both the right and the left border of the Ti- and Ri-plasmid T-DNA, must be bound as a flanking area of the gene being introduced.

The use of T-DNA for the transformation of plant cells has been intensively researched and especially described in EP 120 516; Hoekema, The Binary Plant Vector System Offset-drukkerij Kanters BV, Alblasserdam, 1985, Chapter V; Fraley, et al, *Crit. Rev. Plant Sci.*, 4: 1–46 und An et al, *EMBO J.* (1985) 4: 277–287.

Once the introduced DNA is first integrated in the genome, it is also relatively stable there and as a rule is not usually eliminated. The DNA normally contains a selection marker which gives the transformed plant cells resistance against a biocide or an antibiotic, such as kanamycin, G 418, bleomycin, hygromycin or chloramphenicol, amongst others. The individually used marker should therefore allow the selection of transformed cells as opposed to cells which restrict the introduced DNA.

For the introduction of DNA in a plant host cell, a number of techniques are available. These techniques include transformation with T-DNA using *Agrobacterium tumefaciens* or *Agrobacterium rhizogenes* as transformation media, fusion, injection or electroporation as well as other possibilities. Should Agrobacteria be used for the transformation, the DNA which is to be introduced is cloned in special plasmids, either in an intermediate vector or a binary vector. The intermediary vectors can be integrated based on sequences which are homologous to the sequences in the T-DNA, through homologous recombination in the Ti- or Ri-plasmids. These also contain the Vir-region, necessary for the transfer of the T-DNA. Intermediary vectors cannot be replicated in Agrobacteria. By using a helper plasmid, the intermediary vector can be transferred to *Agrobacterium tumefaciens* (conjugation). Binary vectors can be replicated both in *E. coli* and in Agrobacteria. They contain a selection marker gene and a linker or polylinker, which are framed by the right and left T-DNA border regions. They can be transformed directly in the Agrobacteria (Holsters et al., *Mol. Gen. Genet.* (1978), 163: 181–187). The Agrobacteria serving as host cells should contain a plasmid that carries a Vir-region. The Vir-region is necessary for the transfer of the T-DNA into the plant cells. The plasmid can contain additional T-DNA. The bacterium, so transformed, is used for the transformation of plant cells. For the transfer of DNA into the plant cells, plant explants can be cultivated in a suitable manner with *Agrobacterium tumefaciens* or *Agrobacterium rhizogenes*. From the infected plant material (for example leaf pieces, stem segments, roots and also protoplasts or suspension cultured cells) whole plants can be regenerated in a suitable medium which can contain antibiotics or biocides for selection. The plants so obtained can be tested then for the presence of the introduced DNA. For injection and electroporation, no special conditions on the plasmids are necessary. Simple plasmids, such as for example pUC derivatives, can be used.

The transformed cells grow within the plant in the usual way. These plants can be grown in the normal way and crossed with plants which possess the same transformed genes or other genes. The hybrid individuals resulting from this have the corresponding phenotypic properties.

Expressions and abbreviations

Abbreviations:
bp, Kb=Base pairs, kilobases
d, kd=dalton, kilodalton
SDS=sodium dodecyl sulphate
tris=tris(2-aminoethyl)amine
Expressions
Clone=Cell population that is derived from one of its own mother cells. Descendants are genotypically the same. By cloning, the homogeneity of cell lines can be increased further.
Electrophoresis=A biochemical separation process for separating nucleic acids from proteins according to size and charge.
Endoplasmic reticulum=intercellular membrane channels which serve for transporting of chemical and biochemical substances.
Expression=Activity of a gene.
Gene=Genetic factor; a unit of inheritance, carrier of part information for a particular specified characteristic. Genes consist of nucleic acids (eg DNA, RNA).
Genome=Totality of the gene localised in the chromosomes of the cell.
Internodes=shoot segments which are separated from one another through nodes (for example stems). The leaves are on the nodes.
Internode distance=The distance of various shoot segments from the nodes.
Klenow fragment=Fragment of DNA polymerase I of a size 76,000 d obtained by splitting with subtilisin. Possesses 5'-3' polymerase and 3'-5' exonuclease activity but not the 5'-3' exonuclease activity of the holoenzyme.

Ligation=Enzymatic formation of a phosphodiester bond between 5'-phosphate groups and 3'-hydroxy groups of the DNA.

Linker, Polylinker=Synthetic DNA sequence that contains one or more (polylinker) restriction cutting regions in direct sequence.

Northern blots,=Transfer and fixing of Southern blots, electrophoretically separate RNA or DNA on a nitrocellulose or nylon membrane.

Phenotype=A sum of characteristics which are expressed in an organism as opposed to its genotype.

Phloem=Sieve element of the vascular bundle of a plant through which water flows with dissolved substances.

Promoter=Control sequence of the DNA expression which realises the transcription of homologous or heterologous DNA gene sequences.

Replication=Doubling of the DNA sequence.

Restriction enzymes=Restriction endonucleases which are a sub-group of the endodeoxyribonuclease class (for example EcoRI (specificity G↓AATTC and EcoRII↓CC(A$_T$)GG, from *E. coli*) exhibit a high substrate specificity ( ↓ =splitting position).

Restriction positions =A splitting position which is produced specifically by restriction enzymes.

Termination=Last stage of the protein synthesis, in which the polypeptide chain is completed.

Transformation=Introduction of exogenous DNA of a bacterial species into a receiver cell.

Transcription=Overwriting on an RNA of the genetic information contained in the DNA.

Vectors=Host specific replicatable structures, that take up genes and carry these into other cells. Plasmids can also be used as vectors.

The following plasmids were deposited at the German Collection for Microorganisms (DSM) in Braunschweig, Germany (deposit number):

On 12.2.1990
  Plasmid p35S-CW-INV (DSM 5785)
  Plasmid p35S-CW-INV (DSM 5788)
  Plasmid p33-CW-INV (DSM 5787)
  Plasmid p1700-CW-INV (DSM 5789)
  Plasmid p33-Cy-INV (DSM 5786)
On 20.8.1990
  Plasmid p35S-V-INV (DSM 6142)

The cutting positions are described in the following Example 1.

Figure 2:
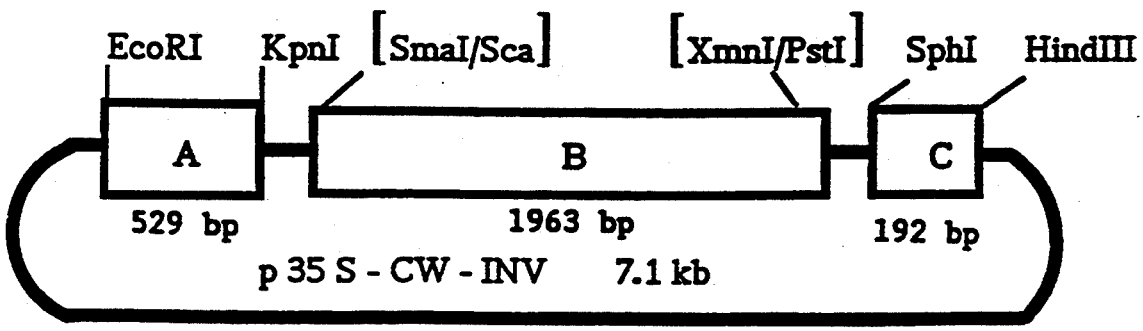

FIG. 2 shows the structure of the 7.1 kb size plasmid p35S-CW-INV. The plasmid contains the following fragments:
  A=Fragment A (529 bp); containing the 35S promoter of the cauliflower mosaic virus (CaMV). It contains a fragment which includes the nucleotides 6909 to 7437 of the CaMV.
  B=Fragment B (1963 bp): contains the nucleotide 923-1159 of a proteinase inhibitor II gene from potato, which are fused via a linker to the suc2 gene from yeast, including the nucleotides +64 to +1765.
  C=Fragment C (192 bp): contains the polyadenylating signal of the gene 3 of the T-DNA of the Ti-plasmid pTiACH5.

The cutting positions are described in the following Example 2.

Figure 3:
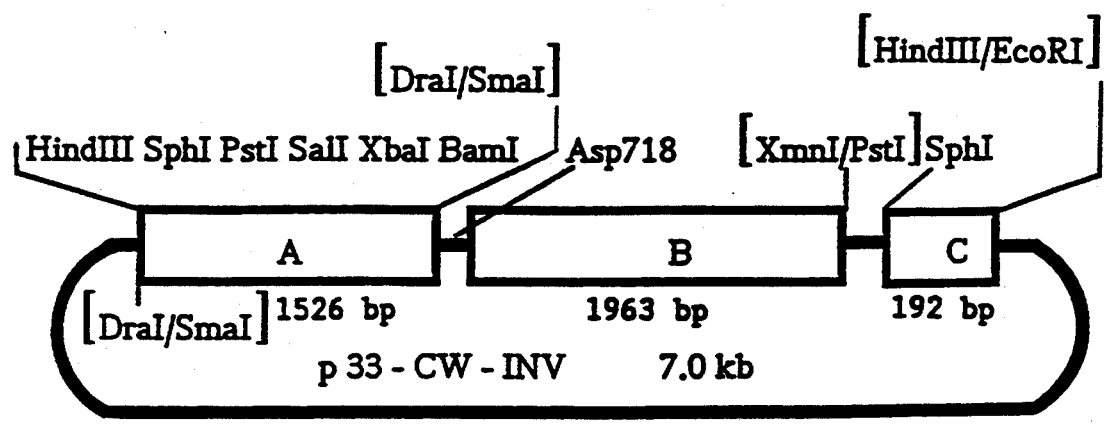

FIG. 3 shows the structure of the 7.0 kb size plasmid p33-CW-INV. The plasmid contains the following fragments:
  A=Fragment A (1526 bp): contains the DraI-DraI fragment (position −1512 to position +14) of the promoter region of the patatin gene B33.
  B & C=Fragment B (1963 bp) and C (192 bp). They correspond to the fragments B & C in plasmid p35S-CW-INV (FIG. 2).

The cutting positions are described in the following Example 3.

Figure 4:
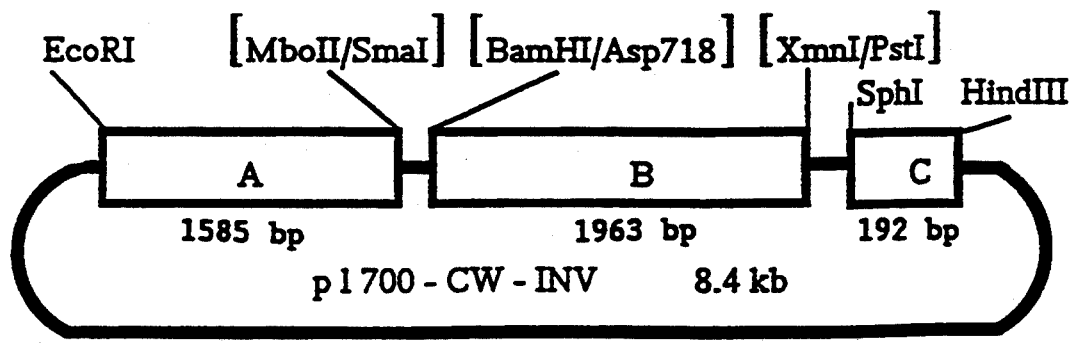

FIG. 4 shows the structure of the 8.4 kb size plasmid p1700-CW-INV. The plasmid contains the following fragments:
  A=Fragment A (1585 bp): contains the EcoRI-MboII fragment of the ST-LS1-gene from potato.
  B & C=Fragment B (1963 bp) and C (192bp): corresponds to the fragments B and C in plasmid p35S-CW-INV (FIG. 2).

The cutting positions are described in the following Example 4.

Figure 1:
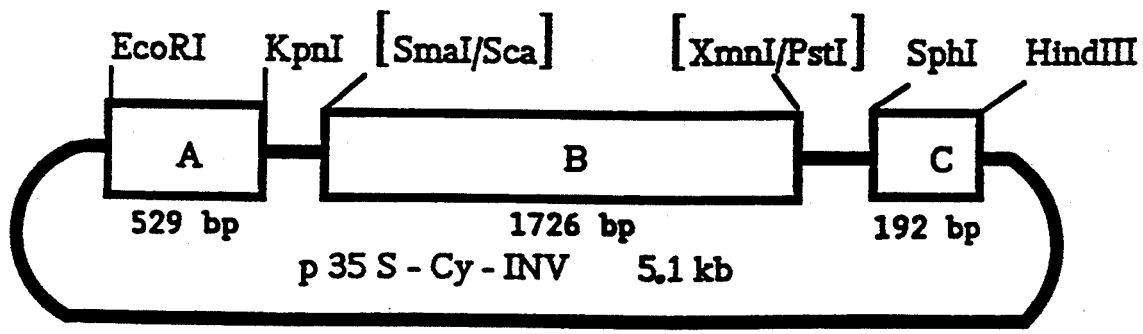
FIG. 1 shows the structure of the 5.1 kb size plasmid p35S-Cy-INV. The plasmid is made up from the following fragments:
  A=Fragment A (529 bp); contains the 35S promoter of the cauliflower mosaic virus (CaMV). It contains a fragment which includes the nucleotides 6909 to 7437 Of the CaMV.
  B=Fragment B (1726 bp); contains 23 nucleotides of a proteinase inhibitor II gene of potato (nucleotides 923-945), which are fused via a linker of 7 base pairs to the suc2 gene from yeast, including the nucleotides +64 to +1765.
  C=Fragment C (192 bp): contains the polyadenylating signal of the gene 3 of the T-DNA of the Ti-plasmid pTiACH5.
Figure 5:
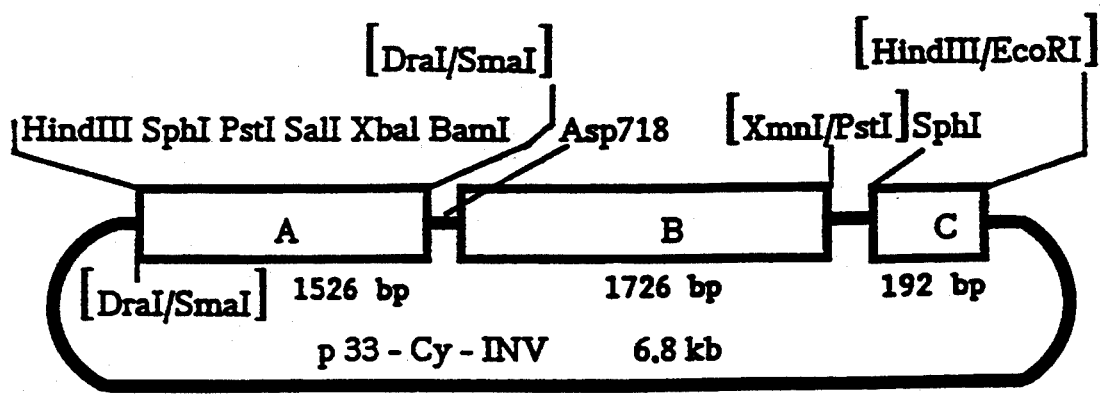

FIG. 5 shows the structure of the 6.8 kb size plasmid p33-Cy-INV. The plasmid contains the following fragments: A=Fragment A (1526 bp): contains the DraI-DraI fragment (position −1512 to position +14) of the promoter region of the patatin gene B33.
  B & C=Fragments B (1726 bp) and C (192 bp): corresponds to the fragments B and C in plasmid p35S-Cy-INV (FIG. 1).

The cutting positions are described in the following Example 5.

Figure 6:
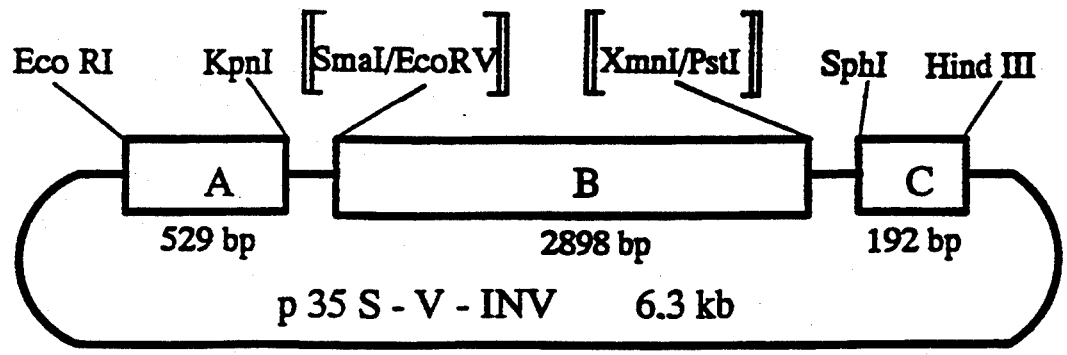

FIG. 6 shows the structure of the 6.3 kb size plasmid p35S-V-INV. The plasmid contains the following fragments:
  A=Fragment A (529 bp): contains the 35S promoter of the cauliflower mosaic virus (CaMV).
  B=Fragment B (2898 bp): contains the nucleotides +707 to +1895 of the sequence of the genomic patatin clone pgT5, a linker of the sequence AGCTTTC and the suc2 gene from yeast (nucleotides +64 to +1765).
  C=Fragment C (192 bp): contains the polyadenylating signal of the gene 3 of the T-DNA of the Ti-plasmid pTiACH5 (nucleotides 11749-11939).

The cutting positions are described in the following Example 6.

Figure 7:
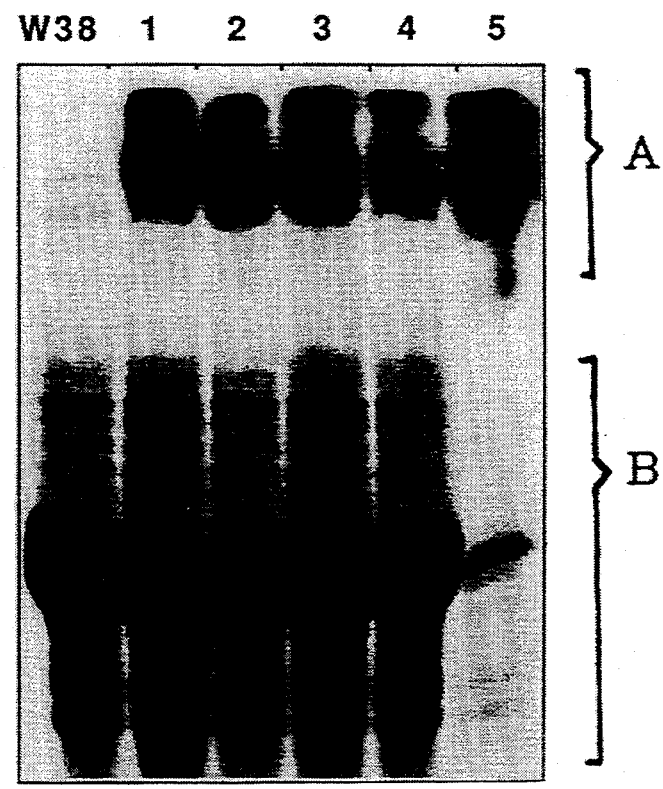

FIG. 7 shows the gel for the in situ evidence of the invertase activity in leaf extracts from 5 independent transgenic tobacco plants (traces 1-5) as well as the absence of such activity in non-transformed plants (trace W38).

A=Gel area containing reducing sugar. The black staining in traces 1–5 show the presence of reducing sugar (invertase activity) in comparison with the control (trace W38).

B=The gel area of the protein fraction.

Figure 8:
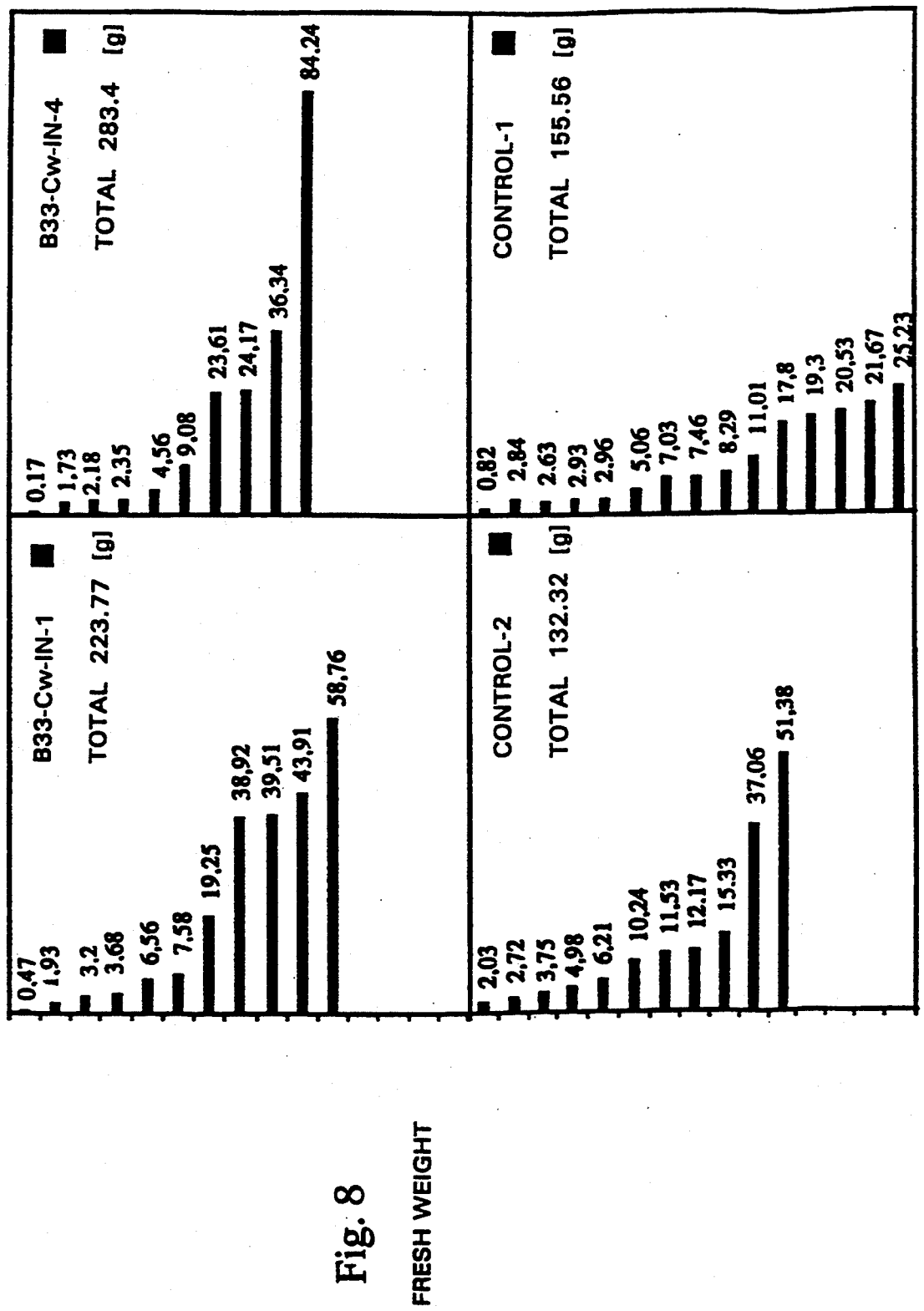

FIG. 8 shows the number, the size distribution (fresh weight) and the total fresh weight of the tubers of two potato plants, transformed with the plasmid p33-CW-INV (left side, plants B33-Cw-IN-4 and B33-Cw-IN-1), as well as two control plants grown under the exact same conditions but not transformed (right side, plants control 1 and control 2). Each vertical column represents a tuber, whose weight in grams is given above the column. The total weight is also given in grams.

Figure 9:
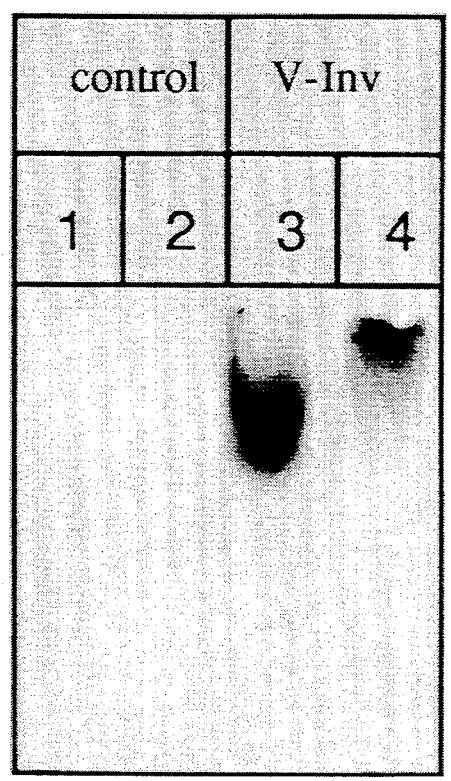

FIG. 9 shows the gel for the in situ evidence of the invertase activity coded from the plasmid p35S-V-INV in the vacuoles of the tobacco plants transformed with this plasmid.

Trace 1: protoplasts of untransformed tobacco plants;
trace 2: vacuoles of untransformed tobacco plants;
trace 3: protoplasts of transgenic tobacco plants;
trace 4: vacuoles of transgenic tobacco plants.

In each trace comparable amounts of protoplasts and/or vacuoles which were normalised via the α-mannosidase activity, were applied. The black staining in traces 3 and 4 show the invertase activity through the formation of reducing sugar. The intensity in both traces is similarly high, which shows the exclusive localising of the invertase in the vacuoles. The invertase activity is not contained in the protoplast and vacuoles of non-transformed tobacco plants (traces 1 and 2).

DESCRIPTION OF THE PREFERRED EMBODIMENT

For a better understanding of this invention the following examples are given. Explanation for these experiments is given as follows:

1. Cloning Vectors

For cloning, the vectors pUC18/19 and pUC118 (Yanisch-Perron et al. , Gene (1985), 33, 103–119) and pMPK110 (Eckes, Dissertation, University of Cologne (1984)) were used.

For the plant transformation, the gene structures were cloned in the binary vectors BIN19 (Bevan, Nucl. Acids Res. (1984), 12, 8711–8720).

2. Bacterial Species

For the pUC-and M13 vectors the E. coli strains BMH71-18 (Messing et al, Proc. Nat. Acad. Sci. USA (1977), 24, 6342-6346) or TB1 was used. For the vectors pMPK110 and BIN19, the E. coli strains TB1 was exclusively used. TB1 is a recombinant-negative, tetracycline resistant derivative of the species JM101 (Yanisch-Perron et al., Gene (1985), 33, 103–119). The genotype of the TB1 species is (Bart Barrel, personal communication): F' (traD36, proAB, lacI, lacZΔM15), Δ(lac, pro), SupE, thiS, recA, Sr1::Tn10(Tc$^R$).

The plant transformation was carried out using Agrobacterium tumefaciens species LBA4404 (Bevan, M., Nucl. Acids Res. 12, 8711-8721, (1984); BIN19 derivative).

3. Transformation of Aqrobacterium tumefaciens.

For Bin19 derivatives, the introduction of the DNA in the Agrobacteria was carried out by direct transformation by the method of Holsters et al. (Mol. Gen. Genet. (1978), 163, 181-187). The plasmid DNA transformed Agrobacteria were isolated by the method of Birnboim and Doly(Nucl. Acids Res. (1979), 7, 1513-1523) and opened up gel electrophoretically by a suitable restriction cleavage.

4. Plant Transformation

A) Tobacco: 10 ml of an overnight culture of Agrobacterium tumefaciens, washed under selection was centrifuged, the supernatant discarded and the bacteria resuspended in the same volume of antibiotic-free medium. In a sterile petri dish, leaf discs of sterile plants, (ca 1 cm$^2$), from which the middle vein had been removed, were bathed in this bacterial suspension. The leaf discs were then compactly laid down in petri dishes which contained MS-medium with 2% sucrose and 0.8% bacto- agar. After two days incubation at 25° C. in the dark, they were transferred to MS-medium which contained 100 mg/l kanamycin, 500 mg/l claforan, 1 mg/l benzylamino-purine (BAP), 0.2 mg/l naphthylacetic acid (NAA) and 0.8% bacto-agar. Growing shoots were put into hormone-free MS-medium with 250 mg/l claforan.

B) Potatoes: 10 small leaves of a sterile potato culture, wounded with a scalpel, were put into 10 ml MS-medium with 2% sucrose which contained 30 to 50 µl of an overnight culture of Agrobacterium tumefaciens, washed under selection. After 3-5 minutes gentle shaking, the petri dishes were incubated at 25° C. in the dark. After two days, the leaves were laid in MS-medium with 1.6% glucose, 2 mg/l zeatinribose, 0.02 mg/l naphthylacetic acid, 0.02 mg/l gibberellic acid, 500 mg/l claforan, 50 mg/l kanamycin and 0.8% bactoagar. After one week incubation at 25° C. and 3000 lux the claforan concentration in the medium was reduced by half.

5. Analysis of the Genomic DNA from Transgenic Plants The isolation of genomic plant DNA was carried out by the method of Rogers and Bendich (Plant Mol. Biol (1985), 5, 69–76).

For DNA analysis 10–20 µg DNA was tested after suitable restriction cleavage with the aid of southern blots by integration of the DNA sequences being analysed.

6. Analysis of the Total RNA from Transgenic Plants

The isolation of the total plant RNA was carried out by the method of Longemann et al (Analytical Biochem (1987), 163, 16-20).

For the analysis, 50 µg samples of total RNA were tested with the use of northern blots to determine the presence of the sought transcripts.

7. Protein extraction

For the extraction of the total protein from plant tissues, tissue pieces were homogenised in protein extraction buffer (25 mM sodium phosphate pH 7.0, 2 mM sodium bisulphite, 2mM phenylmethyl-sulphonyl fluoride (PMSF)), with the addition of 0.1% (w/v) in soluble polyvinylpyrrolidone (PVP).

After filtering through cellulose cell particles were centrifuged off for 20 minutes at 10,000 revolutions per minute and the protein concentration of the supernatant was determined by the method of Bradford (Anal. Biochem. (1976), 72, 248–254).

8Determination of foreign protein with the aid of immunological process (Western-Blot)

Protein extracts were separated using gel electrophoresis in SDS-PAGE (sodium dodecylsulphate-polyacrylamide) gels according to molecular weight. After SDS-PAGE, protein gels were equilibrated for 15–30 minutes in transfer buffer for graphite electrodes (48 g/l tris, 39 g/l glycine, 0.0375% SDS, 20% methanol) and then transferred into the cool room on nitrocellulose filters and separated with 1.3 MA/cm² for 1–2 hours). The filter was saturated for 30 minutes with 3% gelatine in TBS-buffer (20 mM tris/HCl pH 7.5, 55 mM NaCl) and then the filter was incubated for 2 hours with the corresponding anti-serum at a suitable dilution (1:1000–10,000 in TBS buffer) at room temperature. The filter was then washed each time for 15 minutes with TBS-, TTBS-(TBS-buffer with 0.1% Tween 20) and TBS. After washing, the filter was incubated for 1 hour at room temperature with alkaline phosphatase conjugated goat-anti-rabbit (GAR)-antibodies (1:7500 in TBS). The filter was then washed as described above and equilibrated in AP-buffer (100 mM tris/HCl, pH 9.5, 100 mM NaCl 3 mM MgCl₂). The alkaline phosphatase reaction was started through substrate addition of 70 µl 4-nitrotetrazolium (NBT) solution (50 mg/ml NBT in 70% dimethylformamide) and 35 µl 5-bromo-4-chloro-3-indolyl phosphate (BCIP) (50 mg/ml BCIP in dimethylformamide) in 50 ml AP buffer. After 5 minutes, as a rule, the first signals could be seen.

The reaction can be ended by transferring the filters in stop solution (20 mM tris/HCl pH 8.0 with 5 mM EDTA). The reaction was carried out in darkness.

9. Identification of invertase activity

Acid invertase cleaves sucrose into glucose and fructose. The enzyme activity of acid invertase can be shown in plant protein extracts after separation in SDS polyacrylamide gels.

The total protein was extracted from plants as described under Paragraph 7 and treated with 2x native SB buffer (125 mM tris/HCl pH 6.8, 10% 2-mercaptoethanol, 20% glycol, 0.004% bromophenol blue) and added to 0.2% SDS gels. The extracts were not denatured by heating before separation in the SDS polyacrylamide gels. After electrophoretic separation, the gels were washed for a short time in water and incubated for 1 hour at 30° C. in sucrose solution (0.1M sucrose, 0.1M sodium acetate pH 5.0). Then the excess sucrose was separated by several washings (3×5 minutes) with water. The test for reducing sugars was carried out by boiling the gels in TPTC-reaction solution (0.1% 2,3,5-triphenyltetrazolium chloride in 0.5N caustic soda) for 5–10 minutes in a microwave oven. The reaction was stopped in 10% acetic acid. The gels were then dried after washing. An intensive red colouration in the gel showed the presence of reducing sugars (see FIG. 7, under A seen as black staining).

10. Isolation of vacuoles from transgenic and non-transgenic tobacco plants

Protoplasts were prepared from 3 to 4 week old sterile tobacco plants prepared according to known methods (Damm and Willmitzer, *Mol. Gen. Genetics* 217, 15–20 (1988)). Then about 10 million protoplasts were separated from vacuoles by known methods (Boller und Kende, *Plant Physiology* 63, 1123–1132 (1979)). The purity of the vacuoles was confirmed microscopically and by determination of the α-mannosidase activity (Van der Wilden et al., *Plant Physiology* 66, 390–394 (1980)). The invertase activity determination was carried out gel electrophoretically after α-mannosidase equalisation.

In FIG. 8, it is shown that the vacuolar fraction contains a comparable invertase activity, such as the protoplasts treated to the vacuole isolation. The results show that the sub-cellular distribution of the invertase corresponds to the vacuolar marker enzymes of the α-mannosidase.

EXAMPLE 1

Preparation of plasmid p35S-Cy-INV and introduction of the plasmid into the plant genome of tobacco and potato.

Sucrose was split by the enzyme invertase into the two hexoses glucose and fructose. These two hexoses are not chemically equivalent to sucrose and therefore do not lead to a feedback of the unloading of the sucrose from the phloem. A DNA sequence from yeast, that codes for the suc2 gene, is prepared with the of the 35S promoter of the cauliflower mosaic virus, as well as a plant termination signal. The plant termination signal contains the 3'-end of the poly-A side of the octopine synthase gene. The plasmid p35S-Cy-INV consists of the three fragments A, B and C, that are cloned into the cutting positions for restriction enzymes of the polylinker of pUC18 (see FIG. 1).

The fragment A contains the 35S promoter of the cauliflower mosaic virus (CaMV). It comprises a fragment, which includes the nucleotides 6909 to 7437 of the CaMV (Franck et al, (1980) *Cell* 21, 285 to 294 and was isolated as EcoRI-KpnI fragment from the plasmid pDH51 (Pietrzak et al (1986) *Nucleic Acids Res.* 14, 5857–5868) and cloned between the Eco RI-KpnI cutting sites of the plasmid pUC18.

The fragment B contains 23 nucleotides of a proteinase inhibitor II gene from potato (*Solanum tuberosum*) (nucleotides 923–945, Keil et al (1986), *Nucleic Acids Res.* 14, 5641–5650) which is fused via a linker of 7 base pairs with a sequence AGCTTTC to the suc2 gene from yeast, including the nucleotides +64 to +1765 (Taussig and Carlson (1983) *Nucleic Acids Res.* 11, 1943–1954).

The fragment B was inserted as an Sca/XmnI fragment between the SmaI/PstI cutting sites of the polylinker of pUC18, whereby, before the ligation, the 3'-overhanging ends of the PstI cutting site was rendered blunt through incubation with T4-DNA polymerase.

The fragment C contains the polyadenylation signal of the gene 3 of the T-DNA of the Ti-plasmid pTiACH5 (Gielen et al (1984); *EMBO J.* 835–846), and nucleotides 11749–11939, which were isolated as PvuII-HindIII fragment from the plasmid pAGV 40 (Herrera-Estrella et al (1983) *Nature* 303, 209–213) and was cloned, after addition of SphI-linker, into the PvuII cutting site between the SphI-HindIII cutting site of the polylinker of pUC18. The plasmid p35S-Cy-INV has a size of 5.1 kb (see FIG. 1). The part of the plasmid p35S-Cy-INV, containing the fragments A, B and C, was introduced in binary vectors, and using the Agrobacterium system was introduced into tobacco and potato plants. From the transformed cells, intact and fertile plants were regenerated. The analysis of the regenerated plants showed in all analysed tissues (leaf and stem), an invertase activity that was lacking in non-transformed plants. Through immunological processes, it could be shown that this invertase is yeast invertase. This invertase is localised in cytosol and/or cytoplasm. Consequently, transgenic tobacco and potato plants were prepared that contained in all organs and cells a new invertase activity, that arises from the yeast invertase gene introduced in these plants. The regenerated tobacco and potato plants showed a clear difference in relation to the non-transformed plants. Thus the leaves showed a variation in green colour. Further, individual transformed plants variously showed strong growth intensity which led to a shortening of the internode distance in the same leaf. Further, it could be observed that the young leaves turned inwards slightly.

EXAMPLE 3

Preparation of the plasmid p35S-CW-INV and introduction of the plasmid into the plant genome of tobacco and potato.

In a similar process as described under Example 1, the plasmid p35S-CW-INV was prepared, with the modification however, that a signal peptide necessary for the uptake in the endoplasmic reticulum of a plant gene (proteinase inhibitor II gene from potato (Solanum tuberosum), Keil et al 1986) was introduced before the coding sequence of the invertase gene. The plasmid p35S-CW-INV had a size of 7.1 kb and consisted of the three fragments A, B and C which were cloned in the given cutting sites for restriction enzymes of the polylinker of pMPK110 (see FIG. 2).

The fragment A consists of the 35S promoter of the cauliflower mosaic virus (CaMV). It contains a fragment, which includes the nucleotides 6909 to 7437 of the CaMV (Franck et al (1980) *Cell* 21, 285–294) and was isolated as EcoRI-KpnI fragment from the plasmid pDH51 (Pietrzak et al (1986) *nucleic acids Res* 14, 5857–5868) and cloned between the EcoRI-KpnI cutting sites of the plasmid pMPK110.

The fragment B contains the nucleotides 923–1159 of a proteinase inhibitor II gene of potato (*Solanum tuberosum*) (Keil et al (1986) Nucleic Acid Res 14, 5641–5650), which is fused via a linker, with the sequence ACC GAA TTG GGG ATC CCA GCT TTC to the suc2 gene from yeast, which includes the nucleotides +64 to +1765 (Taussig und Carlson (1983) Nucleic Acid Res 11, 1943–1954). Thereby a plant protein N-terminal signal peptide, necessary for the uptake of proteins into the endoplasmic reticulum, is fused to the invertase sequence. The fragment B was introduced as a Sca/XmnI fragment between the SmaI/PstI positions of the polylinker of pMPK110, whereby before the ligation, the 3′ overhanging ends of the PstI cutting sites were rendered blunt by incubation with T4 DNA polymerase.

The fragment C contains the polyadenylation signal of the gene 3 of the T-DNA of the Ti-plasmid pTiACH5 (Gielen et al (1984) *EMBO J.* 835–846, nucleotides 11748–11939) which was isolated as a PvuII-HindIII fragment from the plasmid pAGV 40 (Herrera-Estrella et al (1983) *Nature* 303, 209–213) and cloned, after addition of SphI-linker at the PvuII cutting sites, between the SphI-HindIII cutting sites of the polylinker of pMPK110 (see FIG. 2).

The part of the plasmid p35S-CW-INV, containing the fragments A, B and C was introduced in the plants in an analogous way to that described in Example 1. The analysis of the transgenic plant by means of western-blot and activity tests showed that the invertase coded from suc2 gene is now localised in the extra-cellular space. Transgenic tobacco and potato plants that contain this chimeric gene show, in addition to a shortening of the plants based on the reduced internode distance, a new leaf phenotype that extends from the formation of a mosaic pattern to green and chlorotic areas which stretch up to the formation of necrotic areas. Further, they show strongly reduced root formation.

EXAMPLE 3

Preparation of the plasmid p33-CW-INV and introduction of the plasmid in the potato plant genome In a similar manner to that described in Example 2, however replacing the 35S promoter with the promoter of the class I patatin gene B33 (Rocha-Sosa et al (1989) *EMBO J,* 8, 23–29), the plasmid p33-CW-INV was prepared. The plasmid p33S-CW-INV had a size of 7.0 kb and comprised the three fragments A, B and C which were cloned in the cutting sites for restriction enzymes of the polylinker of pUCl18 (see FIG. 3).

The fragment A contains the DraI-DraI fragment (position −1512 to position +14) of the promoter region of the patatin gene B33 (Rocha-Sosa et al (1989) *EMBO J.* 8, 23–29) which was cloned in the SmaI position of the polylinker of pUCl18.

The fragments B and C correspond to the fragments B and C in the plasmid p35S-CW-INV (see FIG. 2). For cloning of the fragments B and C, the plasmid p35S-CW-INV was digested with Asp718 (partial) and HindIII, the resulting ends of the HindIII cutting sites were completed with DNA polymerase (Klenow fragment) and the fragment containing both intact fragments B and C was separated by means of gel-electrophoresis from other fragments. This fragment was then cloned in the above orientation between the EcoRI cutting site filled with DNA polymerase (Klenow fragment), partially with G +A, and the Asp718 cutting site. By partial filling, the HindIII cutting site was obtained.

The plasmid p33-CW-INV was introduced into the plant, in a similar manner as described in Example 1. In the potato, the chimeric gene leads to a tuber specific expression of the invertase.

Two transgenic potato plants of the species, Desiree, which had been transformed with the plasmid p33-CW-INV, were fully compared under growth conditions, in relation to habit and yield, with control plants which had not been transformed. However, the most significant difference surprisingly, was in the tuber yield. The two plants transformed with the plasmid p33-CW-INV, grown under greenhouse conditions, showed a potato yield of 283 and 223 g respectively, whereas both control plants simply showed a tuber yield of 155 and 132 g of fresh weight, respectively. The determination of the dry weight as well as the total starch content of the potatoes showed the same relative uptake in the plants transformed with the plasmid p33-CW-INV, in comparison with the control plants. This means that the introduction and the tuber specific expression of the plasmid p33-CW-INV in transgenic potato plants has increased the yield of these plants by around 50 to 100% (see FIG. 8). In relation to the size distribution of the tubers, the plants transformed with the plasmid p33-CW-INV yielded significantly more large tubers (see FIG. 8). This means that the introduction and expression of the plasmid p33-CW-INV leads not only to a significant increase of the total potato tuber yield in potato plants, but also to an increase in the size of the individual potato tubers.

EXAMPLE 4

Preparation of the plasmid p1700-CW-INV and introduction of the plasmid into the plant genome of tobacco and potato In a similar manner to that described in Example 2, the plasmid p1700-CW-INV was prepared, but replacing the 35S promoter with the leaf specific promoter of the ST-LS1 gene (Stockhaus et al (1987) *Proc. Natl. Sci. USA* 84, 7943–7947), The plasmid p1700-CW-INV had a size of 8.4 kb and consisted of the three fragments A, B and C that were cloned into restriction sites within the polylinker of pMPK110 (see FIG. 4).

The fragment A contained the EcoRI-MboII fragment of the ST-LS1 potato gene. The position of the MboII side in relation to the published sequence (Eckes et al (1986) *Mol Gen Genetics* 205, 14–22) lies at position 1585 (position +1 to position +1585). This fragment was cloned between the EcoRI-SmaI cutting site of the polylinker of PUC18, in which the overhanging 3' end of the MboII cutting site had been previously rendered blunt by T4-DNA polymerase.

The fragments B and C correspond to the fragments B and C in plasmid p35S-CW-INV (see FIG. 2). For cloning fragments B and C, the plasmid P35S-CW-INV was partially digested with Asp718. The resulting 3' ends were completed with DNA polymerase (Klenow fragment) and the plasmid was then cleaved with HindIII. The fragment containing both intact fragments B and C was separated from other fragments by gel electrophoresis, purified and cloned between the BamHI-HindIII cutting sites of the polylinker of pMPK110. The BamHI cutting site had previously been rendered blunt by filling with DNA polymerase I.

The part of the plasmid p1700-CW-INV, containing fragments A, B and C was introduced into plants in a similar manner to that described in Example 1.

EXAMPLE 5

Preparation of the plasmid p33-Cy-INV and introduction of plasmids in the plant genome of tobacco and potato.

In a similar manner to that described in Example 1, the plasmid p33-Cy-INV was prepared, but replacing the 35S promoter with the promoter of the Class I patatin gene B33 (Rocha-Rosa et (1989) *EMBO J.* 8, 23–29).

The plasmid p33-Cy-INV had a size of 6.8 kb and consisted of three fragments A, B and C which were cloned into the the restriction enzyme cutting sites of the polylinker of pUCl18 (see FIG. 5).

The fragment A contained the DraI-DraI fragment (site −1512 to position +14) of the promoter region of the patatin gene B33 (Rocha-Sosa et al (1989) *EMBO J.* 8, 13–29), which was cloned in the SmaI position of the polylinker of pUCl18. The fragments B and C correspond to the fragments B and C in plasmid p35S-Cy-INV. For cloning the fragments B and C, the plasmid p35S-Cy-INV was digested with HindIII, the resulting 3' end being completed with DNA polymerase (Klenow Fragment). The plasmid was partially digested with Asp 718 and both intact fragments B and C were separated by gel electrophoresis from other fragments. These fragments were then cloned between the Asp718 and the EcoRI cutting sites of the polylinker of pUCl18 which is filled with DNA polymerase, partially with G+A. By the partial filling, the HindIII cutting sites were obtained.

The plasmid p33-Cy-INV was introduced in a similar manner as described in Example 1 into the plants.

EXAMPLE 6

Preparation of the plasmid p34S-V-INV and introduction of the plasmid in the plant genome of tobacco In a similar manner to that described in Example 1, the plasmid p35S-V-INV was prepared, with the modification that, in front of the coding sequence of the invertase gene, a peptide of a plant gene (patatin-gene pgT5 from potato, Rosahl et al., Mol. General Genetics 203, 214–220), which is necessary for the direction of the invertase protein into the vacuole, was fused. The plasmid p35S-V-INV had a size of 6.3 kb and consisted of the three fragments A, B and C, which were cloned into the given cutting sites of the polylinker of pUC 18 (see FIG. 6). Fragment A (529 bp) contains the 35S promoter of the cauliflower mosaic virus (CaMV). The fragment includes the nucleotides 6909 to 7437 of the CaMV (Franck et al., *Cell* 21, 285–294), and was isolated as Eco RI-Kpn I fragment from the plasmid pDH51 (Pietrzak et al., *Nucleic Acid Research* 14, 5857–5868) and cloned between the Eco RI-Kpn I cutting sites of the polylinker of the plasmid pUC 18 (see FIG. 6).

Fragment B contains the nucleotides 707 to 1895 of the sequence of the genomic patatin clone pgT5 (Rosahl et al., 1986), which is fused via a linker with the sequence AGCTTTC to the suc 2 gene from yeast, which includes the nucleotides +64 to +1765 (Taussig und Carlson, (1983) *Nucleic Acid Res.* 11, 1943–1954). In this way, a peptide responsible for the direction of proteins in the vacuoles of higher plants and which has a corresponding vacuolar N-terminal targeting signal, is fused to the invertase sequence. The fragment B was introduced as an EcoRV-XmnI fragment, between the SmaI/PstI cutting sites of the polylinker of pUC 18 (see FIG. 6), in which before ligation, the 3'-overhanging ends of the PstI cutting site were rendered blunt by incubation with T4-DNA-polymerase.

Fragment C (192 bp) includes the polyadenylation signal of the T-DNA gene 3 of of the Ti-plasmid pTiACH5 (Gielen et al, *EMBO J.* 3, 835–846) with the nucleotides 11749–11939, which was isolated as the PvuII-HindIII fragment from the plasmid pAGV40 (Herrera-Estrella et al (1983) *Nature* 303, 209–213) and after addition of SphI linkers, was cloned to the PvuII cutting sites between the SphI-HindIII cutting sites of the polylinker of pUC 18.

Analysis of the resulting transgenic tobacco plant by means of invertase activity tests showed that the invertase coded from the suc2 gene is now localised in the vacuole (see FIG. 9). Transgenic tobacco plants showed, in addition to a shortening of the plants, a new leaf phenotype. This was seen by the fact that in older leaves, chlorotic areas developed, beginning at the leaf tips.

We claim:

1. A plasmid comprising a class I patatin promoter operably linked to a DNA sequence encoding a polypeptide consisting of a signal peptide fused to invertase, wherein the signal peptide is functionally capable of directing the translocation of the invertase to a plant cell apoplast.

2. A plasmid according to claim 1, wherein the class I patatin promoter is a potato tuber specific promoter.

3. A plasmid according to claim 1, wherein the gene encoding invertase is a SUC2 invertase gene from yeast.

4. A plasmid according to claim 2, wherein the patatin promoter is a promoter of the class I patatin gene B33.

5. A plasmid according to claim 1, wherein the DNA sequence of the signal peptide comprises at least the portion of a proteinase inhibitor II gene of *Solanum tuberosum* which is functionally capable of directing the translocation of the invertase to the plant cell apoplast.

6. A potato cell transformed with a plasmid according to claim 1.

7. A potato plant containing a plasmid according to claim 1.

8. A method for producing potato plants having an increased yield comprising transforming potato plants using the plasmid according to claim 1.

9. Plasmid p33-CW-INV (DSM 5787).

10. A potato plant containing a plasmid according to claim 9.

11. A method for the preparation of potatoes with an increased dry weight of turbers comprising transforming plants with the plasmid according to claim 9.

12. A method for the production of transgenic potato plants, characterized in that the transgenic potato plants have an increased yield, comprising the following steps:
  a) producing an expression cassette having the following sequences:
      i) a class I patatin promoter, operably linked to
      ii) a DNA sequence encoding invertase; fused to
      iii) a DNA sequence of a signal peptide, wherein the signal peptide is functionally capable of directing the translocation of the invertase to a plant cell apoplast;
  b) transferring the expression cassette into potato cells thereby producing transformed potato cells; and
  c) regenerating whole, intact transgenic potato plants from the transformed potato cells.

* * * * *